United States Patent [19]

Woolcock

[11] Plant 4,278

[45] Jul. 11, 1978

[54] MINIATURE ROSE PLANT

[76] Inventor: Edward P. Woolcock, 1015 Acacia Dr., Placentia, Calif. 92670

[21] Appl. No.: 830,354

[22] Filed: Sep. 2, 1977

[51] Int. Cl.[2] ..... A01H 5/00

[52] U.S. Cl. ..... Plt./9

[58] Field of Search ..... Plt./7, 9

*Primary Examiner*—Robert E. Bagwill
*Assistant Examiner*—James R. Feyrer

[57] ABSTRACT

This invention relates to a new variety of bush type miniature rose primarily distinguished by the soft pink coloring of its buds and flowers.

1 Drawing Figure

1

The present invention relates to a new and distinct variety of hardy, dwarf, bush type rose plant of the miniature class; the variety being primarily characterized — as to novelty — by soft pink buds and flowers which in general color effect are similar to Baby Betsy McCall (miniature — U.S. Plant Pat. No. 1,984, expired).

The variety is further characterized by:

An abundance of bloom, with flowers borne singly or several to the stem in loose clusters.

Faint but sweet fragrance.

A plant which is vigorous, of rounded somewhat spreading shape with small matt foliage with pointed leaflets; the buds and flowers being similar in form and side to Judy Fischer (miniature — U.S. Plant Pat. No. 3,137).

The plant, which has a normal height of 10–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me in my home garden, then located in Garden Grove, Orange County, Calif., under conditions of careful control and observation, as a cross between Little Darling (U.S. Plant Pat. No. 1,581, Floribunda, expired) as the seed parent and Magic Wand (miniature — not patented) as the pollen parent.

Subsequent to origination of the variety I successfully asexually reproduced it, in my garden located as aforesaid (also propagated by Pixie Treasures, 4121 Prospect Avenue, Yorba Linda, Calif.) by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety name: PEACHES 'N CREAM.

2

Flowers borne: Singly and several together (three to five) on slender wirey stems.

Quantity of bloom: Abundant both outside and in greenhouse.

Bud: Penduncle — medium length; slender but sturdy; erect; medium green, sometimes tinted bronze (outdoors); Hairs — few, very tiny. Before calyx breaks; size — small. Form — medium long; pointed with several foliaceous appendages and few or no hairs on surface of bud; with foliaceous parts extending beyond the tip of the bud equal to one-half or more of its length. Color — medium green, occasionally tinted with bronze (outdoors). As calyx breaks, color — soft pink, becoming white to greenish white toward base. Opening: opens well in all weather.

Bloom: size when fully open — small, averaging about 35 mm (1¼–1⅜inches). Petalage — double — averaging about 35–40 petals — sometimes more, arranged regularly plus several small petaloids. Form — full at first, becoming rounded with high center, with petals rolled loosely outward, and later at maturity full with petals folded at edge to give a pointed effect and rolled loosely outward and downward.

Petals: Fairly thick; satiny on inside and on outside surface. Shape — outside petals, broad lanceolate with rounded tip; intermediate — broad lanceolate with acute tip; inside petals, lanceolate with acute tip.

Color: Newly opened flower from a plant grown in plastic greenhouse, July 1977, at Sequoia Nursery, Visalia, Calif.

*Outside petal.*—Outside surface — near Venetian Pink 420/$_1$ becoming white to greenish toward base. Inside surface — near Venetian Pink 420, with tiny, slightly darker veining and shading into near white and light greenish color at base.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — soft delicate pink. Three days open — color similar to newly opened flowers but lighter color. Behavior — opens well in all weather. Spent petals drop off. Flower longevity (June 1977) — plant in pot 4–6 days or longer. Cut flowers at living room temperature 3–5 days or longer.

Reproductive organs:

*Stamens.*—Few or none.

*Filaments.*—Varying length, (if present).
*Anthers.*—Usually none.
*Pollen.*—Little or none.
*Pistils.*—Usually malformed.
*Styles.*—Uneven — bunched.
*Ovaries.*—All enclosed in calyx.
*Hips.*—None.
*Sepals.*—Permanent; spear shaped; recurved.
*Seed.*—None.

Foliage:

*Leaves.*—Compound of five (sometimes three or seven) leaflets; quite small; leathery; matt.
*Leaflets.*—Shape: broad, lanceolate; apex acute; base rounded or rounded acute. Margin serrate.
*Color.*—Medium green; new growth — normal (medium) green (sometimes tinted bronze — outdoors).
*Rachis.*—Medium strength; upper side may have a few tiny short hairs, grooved; underside fairly thorny — of varying length but all curving downward.
*Stipules.*—Medium long; medium width; medium length narrow points which turn out usually at about 45° or less.

Growth:

*Habit.*—Dwarf; bushy; rounded; much branched;
*Growth.*—Free vigorous; internodes short.
*Canes.*—Medium; slender; sturdy.
*Main stems.*—Color: medium green.

*Thorns.*—Average; slender; hooked slightly downward; color; brown. Prickles — none. Hairs — none.
*Branches.*—Color: medium green. Thorns: average number; long; slender; inclined slightly downward. Medium to long oval base. Prickles; none. Hairs — none.

The miniature rose plant and its flowers as herein described may vary in slight detail due to climatic, soil and cultural conditions under which the variety may be grown; the present description being of the variety as grown and observed in plastic greenhouse at Visalia, Calif.

The following is claimed:

1. A new and distinct variety of miniature rose plant of hardy, dwarf, bushy, rounded much branched habit, substantially as illustrated and described, characterized by buds and flowers which are soft pink in color, with slight coral tone, the depth or shade of color may vary as influenced by the temperature and light intensity, the buds and flowers resembling Judy Fischer (miniature — U.S. Plant Pat. No. 3,137) in size and shape; and further characterized by a plant which is vigorous and compact, easy to propagate from cuttings, with an abundance of small to medium size matt foliage and an abundance of flowers borne singly or several to the stem in loose clusters.

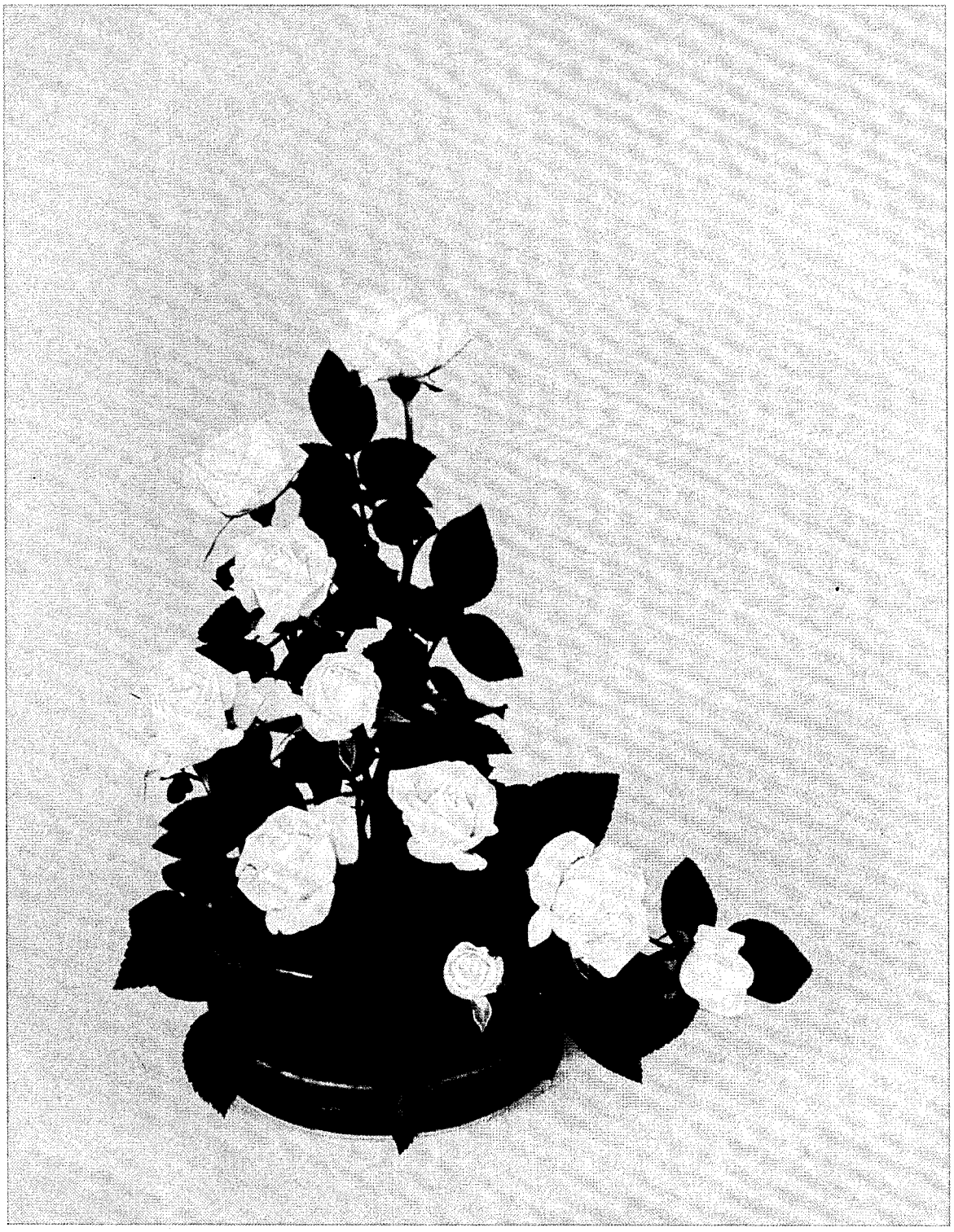

* * * * *